United States Patent [19]

Herb

[11] 4,180,567

[45] Dec. 25, 1979

[54] IRON PREPARATIONS AND METHODS OF MAKING AND ADMINISTERING THE SAME

[75] Inventor: John R. Herb, Bethlehem, Pa.

[73] Assignee: Pharmachem Corporation, Bethlehem, Pa.

[21] Appl. No.: 830,035

[22] Filed: Sep. 2, 1977

[51] Int. Cl.$^2$ .............................................. A61K 31/70
[52] U.S. Cl. ..................... 424/180; 536/113; 536/3; 536/56; 536/103
[58] Field of Search ..................... 536/113, 103, 3, 63, 536/56; 424/180

[56] References Cited

U.S. PATENT DOCUMENTS 2,820,740  1/1958  Londoun et al. .................... 424/180
3,234,209  2/1966  Floramo et al. ..................... 536/113

FOREIGN PATENT DOCUMENTS 83284  7/1974  Japan ........................................ 424/180

Primary Examiner—Johnnie R. Brown
Assistant Examiner—Blondel Hazel
Attorney, Agent, or Firm—Miller & Prestia

[57] ABSTRACT

The present invention is directed to a process for preparing an iron complex with polymeric polyhydroxy compounds such as dextran, hydrogenated dextran, dextrin, carboxyalkyl dextran, carboxyalkyl cellulose, alginates and the like, and therapeutic preparations thereof. The invention also relates to the products obtained, and to their administration to warm-blooded mammals.

5 Claims, No Drawings

IRON PREPARATIONS AND METHODS OF MAKING AND ADMINISTERING THE SAME

BACKGROUND OF THE INVENTION

The present invention relates to an iron preparation suitable for use in mammals and to a process for the manufacture of such preparations. More paticularly, the present invention relates to the complexes formed by iron and an activated polymeric polyhydroxy compound.

It has heretofore been known to use an iron-dextran complex to increase reproduction at pig breed by counteracting the development of anemia at an early stage, (Andersson N. S. E., Acta med. scand. 138 (1950) suppl. 241.1–17).

It is well known that a number of polyvalent metallic ions such as iron will form complexes with polyhydroxy compounds such as polyhydric alcohols. However, on any substantial change in pH, the shift in equilibrium may cause the complex to decompose and the metallic ion in the presence of hydroxyl ion may tend to form a precipitate. This materially reduces the usefulness of these complexes for holding metallic ions in solution over varying pH ranges, and accordingly limits the usefulness of such complexes for trace metal metabolism in the body of mammals, including the human body.

In the preparation of iron complexes, it is known that the iron should be in the trivalent form since ferrous compounds do not give the desired stability of the ferric compounds. Ferric chloride is commonly utilized as a source for ferric ions. However, since ferric chloride is difficult to handle because it is corrosive to the conventional metal containers utilized in large scale operations, it presents certain disadvantages. Furthermore, in the conventional process of preparing iron-dextran complexes, precipitants, such as methanol, ethanol, isopropanol, acetone and methylethyl ketone are utilized in order to isolate and obtain the desired product which undergoes still further isolation and purification processes to obtain a suitable compound for use as an injectable.

U.S. Pat. No. 2,885,393 discloses the preparation of dextran-iron complexes utilizing either a hydrolysis mixture of dextran of fractionated dextran.

U.S. Pat. No. 3,574,184 discloses a process wherein colloidal ferric hydroxide is preformed under controlled conditions and then reacted with dextrans to form a ferric hydroxide-dextran complex.

U.S. Pat. No. 2,820,740 discloses a method for forming hydrogenated dextrans and the formation of ferric hydroxide - partially depolymerized dextran complexes.

U.S. Pat. No. 3,151,107 discloses a process for preparing carboxy alkyl dextrans and the preparation of water soluble iron complexes of the carboxy alkyl dextrans.

The dextrans and dextrins of such an average molecular weight are obtained by known methods, such as by growing under carefully controlled conditions of temperature, appropriate organisms in a suitable nutrient medium containing a high proportion of sucrose or by controlled acid hydrolysis of native dextrans and dextrins or they may be obtained synthetically, as described for instance in U.S. Pat. No. 3,022,221 and Rompp Chemielexikon, 4th edition, 1958, column 1121–1122.

The hydrogenated dextrans and dextrins may be produced according to known methods, such as by subjecting a dextran or dextrin of the average molecular weight defined hereinabove to reaction with sodium boro-hydride in an aqueous medium or by catalytic hydrogenation as described for instance in U.S. Pat. Nos. 2,807,610 or 3,022,221 or in J. Am. Chem. Soc. 74 (1952) pgs. 2126–2127.

Algin is a polysaccharide which is nearly a pure polymer of uronic acid arranged in a long linear chain, and is unique among the water soluble gums. The principal source of algin is Macrosystis Pyrifers, a giant kelp. The most common algin compound is sodium alginate. The modern mechanized algin processing plant meets the requirements of the Food, Pharmaceutical and Industrial Users for a pure, clean uniform water soluble gum. Pharmaceutical grades of alginate are entirely free of cellulose, form water soluble salts with various metals, and have been used as suspending agents and as protective colloids in many pharmaceuticals. In some systems, such as those containing penicillin, sulfa drugs and colloidal sulfur, they provide exceptional stability because of their action as protective colloids.

SUMMARY OF THE INVENTION

The present invention relates to a novel process for preparing organic complex ferric compounds of iron and polymeric polyhydric compounds, to the products, and to the administration of such products to warm-blooded mammals. More particularly, the present invention relates to the preparation of complex ferric compounds by the utilization of a dialyzed iron solution and an activated polyhydric compound such as a dextran, dextrin, alginate or carboxyalkyl cellulose.

The dextrans within the scope of this invention include depolymerized dextrans, hydrogenated dextrans, carboxyalkyl dextrans and the like.

In carrying out the process of the present invention, a solution of dialyzed iron is mixed with a solution of an activated polyhydroxy compound, at an elevated temperature, preferably 75°–100° C., to form the desired complex.

It has been surprisingly found that treatment of the polyhydric compound with a base such as sodium hydroxide at a basic pH, preferably about 8.0–11.5, causes the polyhydric compound to become activated so as to form a novel complex with an iron compound, such as in the form of dialyzed iron. The activation reaction is carried out for a sufficient time and temperature to activate the polyhydric compound but short of substantial degradation of the compound. The time of the reaction is dependent upon the type of compound, pH and temperature utilized. The temperature utilized is not critical but a temperature range of 85°–100° C. was found to be advantageous to effect a rapid activation. A reaction time of about 0.5–1.0 hours in many cases when a temperature range of 85°–100° C. was used, is found to be sufficient. Prolonged treatment causes a reduction of yield due to degradation of the polyhydric compound.

It has been further found that when dextran or dextrin is hydrogenated by the utilization of sodium boro-hydride, there is simultaneously formed an activated compound which may be utilized without any further treatment with a base.

Dialyzed iron solutions are commercially available as salt-free solutions of ferric hydroxide. The ferric hydroxide may be prepared from a conventional ferric compound such as ferric chloride, ferric nitrate, ferric citrate and the like.

It has been found that in producing the stable and soluble complexes of the present invention, the aqueous solution of the dialyzed iron employed is conveniently in a range of concentration such that the final solution of the complex is about 0.9 to 2 molar in the metal, that is, 0.9 to 2 gram atom of the metal per liter of solution, usually about 0.9 to 2 molar. The molar concentration of the polyhydric compound employed with relation to the molar concentration of the iron in the final solution is preferably at least 1:1.4 and preferably at least 1:1.5.

The injectable solutions prepared according to the present invention preferably contain 50–150 milligrams of iron per milliliter, especially about 100 milligrams of iron per milliliter. It is desirable that the iron concentration in the injection solution should be as high as possible in order that the injected volume be small. In some cases, however, a less concentrated preparation may be more suitable.

The presence of an amount of dextran not only assists in the maintenance of the stability of the iron complex but permits the incorporation, if desired, of a resorption retarding agent, by preventing the resorption retarding agent from becoming part of the complex. Also, dextran itself functions as a resorption retarding agent.

The production of ampoule solutions for parenteral administration can be effected by merely adjusting the concentration of the reaction mixture. Optionally, resulting solutions are heated to a temperature between 40° and 100° C., preferably, between 60° and 80° C., and the pH of the solutions is adjusted in a range of 5–10, preferably 5.2–7. After the optional addition of a suitable resorption retarding agent, water is added to the solutions until an iron content suitable for therapy of 50 to 150 mg/ml. is obtained, and the solutions are filtered and poured into ampoules and subsequently sterilized.

Suitable basic compounds for the subsequent adjustment of the pH value are preferably sodium compounds, e.g, sodium hydroxide, sodium carbonate and sodium bicarbonate, although the corresponding potassium or ammonium compounds may likewise be employed.

The complex of the present invention can also be prepared for oral administration in the form of a pill or tablet. Such pill or tablet can be prepared by removal of water from the aqueous solution of the complex without adversely affecting the complex, e.g., by flash distillation, or by precipitating the complex from solution by means of ethanol. The solid isolated complex is dried, and excess sugar may be added if desired. Preferably, sodium acetate is also added to the pill composition for buffering purposes.

The invention will be more fully understood with reference to the following Examples:

EXAMPLE 1

300 ml of distilled water were added with stirring to 80 g of dextran and the mixture is stirred until a solution is obtained. 1 ml of a 50% solution of sodium hydroxide was added to the solution and the solution was diluted to 500 ml with water (pH 10.5 to 11.3). The mixture was then heated to a temperature of 95°–100° C. and agitated for 60 minutes. The mixture containing the activated dextran was allowed to cool to room temperature and then 500 ml of 8% dialyzed iron solution (Fe(OH)$_3$) having a pH of 4.1 and a specific gravity of 1.096 were added with stirring.

Upon addition of the 8% dialyzed iron solution, the mixture was heated to a temperature between 95°–100° C. and concentrated to a volume of 350 ml and then permitted to cool. The mixture at a concentration of 350 ml had an iron concentration of 9.86%.

The pH of the reaction mixture was adjusted to 5.2–6.5. The solution was filtered through a sterile filter, placed in ampoules and sterilized in an autoclave.

EXAMPLE 2

A. Preparation of Hydrogenated Dextran 200 grams of sodium borohydride dissolved in water (pH over 10) were added to a 10% solution containing 10 pounds of dextran. The mixture was allowed to stand at room temperature for 5 hours with occasional stirring. The pH of the mixture during that period was 10.2–10.8. The product was then acidified with 30% acetic acid. The acidified mixture was passed through a column of cation exchange resin, and the effluent therefrom was passed through a column of anion exchange resin. Methyl alcohol was added with stirring to the deionized solution to give a solution containing 60% of methyl alcohol by volume. After standing for 24 hours at 25° C., the supernatant solution was decanted from the precipitated reduced dextran. The product was dried at 100° C. in vacuum for 2 hours. The resultant hydrogenated dextran was non-reducing to Somogyi reagent.

B. Preparation of Iron Complex

Into a vessel containing a stirrer and a thermometer, were charged 250 ml of distilled water and 80 g of the hydrogenated dextran of Part A. The mixture was diluted to 500 ml with distilled water and 500 ml of an 8% dialyzed iron solution were added dropwise over a period of 60 minutes. After addition of the dialyzed iron solution was completed, the solution was concentrated at atmospheric pressure at a temperature of 95°–100° C. with agitation to 400 ml and filtered. The resultant solution was concentrated to 350 ml and filtered. The resultant solution was concentrated to 350 ml and it was noted that it had a pH of 4.8. After adjustment to pH 5.2 to 6.5 with alkali it had an iron content of 10.4%.

EXAMPLE 3

300 ml of distilled water were added with stirring to 80 g of carboxymethyl dextran obtained by the process described in U.S. Pat. No. 3,151,107. The mixture was stirred until a solution was obtained. 1 ml of a 50% solution of sodium hydroxide was added to adjust the pH to 10.5–11.3 and the solution was diluted to 500 ml with water. The mixture was then heated to a temperature of 95°–100° C. and agitated for 60 minutes. The mixture containing the activated carboxymethyl dextran was allowed to cool to room temperature and then 500 ml of 8% dialyzed iron solution (FE(OH)$_3$) having a pH of 4.1 and a specific gravity of 1.096 were added with stirring.

Upon addition of the 8% dialyzed iron solution, the mixture was heated to a temperature between 95°–100° C. and then permitted to cool. The mixture contained the iron-carboxymethyl dextran complex.

EXAMPLE 4

300 ml of distilled water were added with stirring 80 g of carboxymethyl cellulose and the mixture were stirred until a solution was obtained. 1 ml of a 50% solution of sodium hydroxide was added to adjust the pH to 10.5–11.3 and the solution was diluted to 500 ml with water. The mixture was then heated to a temperature of 95°–100° C. and agitated for 60 minutes. The mixture containing the activated carboxymethyl cellulose was allowed to cool to room temperature and then 500 ml of 8% dialyzed iron solution (FE(OH)$_3$) having a pH of 4.1 and a specific gravity of 1.096 were added with stirring.

Upon addition of the 8% dialyzed iron solution, the mixture was heated to a temperature between 95°–100° C. and then permitted to cool. The mixture contained the iron carboxymethyl cellulose complex.

It is recognized that various modifications may be made in the invention described herein. In its broadest aspect, the invention contemplates that the iron complexes can be formulated for use parenterally, intraveneously or orally, with or without the use of additives and other medicaments.

I claim:

1. In a process for preparing an iron complex from a polymeric polyhydric compound selected from the group consisting of dextran, depolymerized dextran, dextrin, carboxyalkyl dextran, carboxyalkyl cellulose and alginates and a solution of an iron compound in a basic medium and at a temperature of 75°–100° C., the improvement which comprises activating said polyhydric compound by pretreatment with a base at a basic pH for about 0.5 to 1.0 hours and at a temperature of 85°–100° C., and then admixing said activated polyhydric compound with an aqueous solution of an iron compound consisting essentially of dialyzed iron.

2. The process according to claim 1, wherein said dialyzed iron solution is a dialyzed salt-free solution of ferric hydroxide.

3. The process according to claim 1, wherein said polyhydric compound is dextran and said dextran is employed in a molar concentration with relation to the iron of at least 1:1.3.

4. The process according to claim 1, wherein said dialyzed iron solution is a dialyzed salt-free solution of ferric hydroxide.

5. A stable injectable iron dextran solution which is prepared by pretreating dextran in an aqueous solution with a base at a basic pH for about 0.5 to 1.0 hours at a temperature of 85°–100° C., so as to activate the dextran, adding to said solution a dialyzed aqueous solution of ferric hydroxide and then heating the mixture to a temperature between 95°–100° C., at a basic pH whereby a solution of an iron-dextran complex is obtained that can be utilized without further treatment.

* * * * *